(12) United States Patent
Miller et al.

(10) Patent No.: US 7,915,469 B2
(45) Date of Patent: Mar. 29, 2011

(54) HYDROCARBON CONVERSION PROCESSES USING UZM-26 AND UZM-26X CRYSTALLINE MICROPOROUS ZEOLITIC COMPOSITIONS

(75) Inventors: Mark A. Miller, Niles, IL (US); Gregory J. Lewis, Santa Cruz, CA (US)

(73) Assignee: UOP LLC, Des Plaines, IL (US)

( * ) Notice: Subject to any disclaimer, the term of this patent is extended or adjusted under 35 U.S.C. 154(b) by 289 days.

(21) Appl. No.: 12/335,648

(22) Filed: Dec. 16, 2008

(65) Prior Publication Data
US 2010/0152510 A1    Jun. 17, 2010

(51) Int. Cl.
*C07C 5/66* (2006.01)
*C07C 2/12* (2006.01)
*C07C 5/27* (2006.01)
*C10G 73/02* (2006.01)

(52) U.S. Cl. ........... 585/467; 585/418; 585/533; 208/27

(58) Field of Classification Search .................. 585/467, 585/418, 533; 208/27
See application file for complete search history.

(56) References Cited

U.S. PATENT DOCUMENTS

| | | | |
|---|---|---|---|
| 4,310,440 A | 1/1982 | Wilson et al. | 252/435 |
| 4,440,871 A | 4/1984 | Lok et al. | 502/214 |
| 5,157,196 A | 10/1992 | Crossland et al. | 585/720 |
| 5,157,197 A | 10/1992 | Cooper et al. | 585/726 |
| 6,776,975 B2 | 8/2004 | Wilson et al. | 423/713 |
| 2005/0095195 A1 | 5/2005 | Lewis et al. | 423/705 |

OTHER PUBLICATIONS

U.S. Appl. No. 12/335,657, filed Dec. 16, 2008, Mark A. Miller et al.

*Primary Examiner* — Thuan Dinh Dang
(74) *Attorney, Agent, or Firm* — Frank S Molinaro

(57) ABSTRACT

This invention relates to hydrocarbon conversion processes using crystalline zeolitic compositions designated the UZM-26 and UZM-26X. UZM-26 is a microporous three-dimensional zeolitic composition that is derived from UZM-26P (an as synthesized layered composition) by calcination. UZM-26X is a microporous three-dimensional zeolitic composition that is derived from UZM-26PX by calcination, where UZM-26PX is an ion-exchanged form of UZM-26P.

2 Claims, No Drawings

HYDROCARBON CONVERSION PROCESSES USING UZM-26 AND UZM-26X CRYSTALLINE MICROPOROUS ZEOLITIC COMPOSITIONS

FIELD OF THE INVENTION

This invention relates to hydrocarbon conversion processes using two species of a new family of crystalline aluminosilicate compositions designated the UZM-26 family. These include the species UZM-26 and UZM-26X, which have unique structures. UZM-26 is a microporous three-dimensional zeolitic composition that is derived from UZM-26P by calcination. UZM-26X is a microporous three-dimensional zeolitic composition that is derived from UZM-26PX by calcination, where UZM-26PX is an ion-exchanged form of UZM-26P.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

Applicants have successfully prepared a new family of crystalline aluminosilicate compositions designated UZM-26. The family includes an as-synthesized layered composition designated UZM-26P; a calcined three dimensional microporous zeolitic composition designated UZM-26; an ion-exchanged form of the as-synthesized composition designated UZM-26PX; and a calcined three dimensional microporous zeolitic composition of the ion-exchanged composition, designated UZM-26X. The topologies of these UZM-26 family members are distinct from each other and other aluminosilicate species in the prior art. The layered composition can also be expanded and exfoliated by using cationic surfactants. The as-synthesized layered composition, UZM-26P, is prepared using a structure directing agent such as hexyltrimethylammonium hydroxide, $[CH_3(CH_2)_5NMe_3]^+OH^-$, plus an alkali earth metal such as $Ca^{2+}$ using the Charge Density Mismatch Process for synthesizing zeolites as described in US Patent Application Publication No. 2005/0095195.

SUMMARY OF THE INVENTION

As stated, the present invention relates to hydrocarbon conversion processes using UZM-26 and UZM-26X. Accordingly, one embodiment of the invention a hydrocarbon conversion process comprising contacting a hydrocarbon stream with a crystalline microporous zeolitic composition at hydrocarbon conversion conditions to give a converted product, the crystalline zeolitic microporous composition having a three-dimensional framework composed of at least tetrahedral $SiO_2$ units and an empirical composition on an anhydrous basis expressed by the empirical formula of:

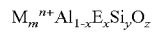

$$M_m^{n+}Al_{1-x}E_xSi_yO_z$$

where M is at least one exchangeable cation selected from the group consisting of hydrogen ion, alkali, alkaline earth, and rare earth metals, "m" is the mole ratio of M to (Al+E) and varies from 0.05 to about 10.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation:

$$z=(m\cdot n+3+4\cdot y)/2$$

and is characterized in that it has the x-ray diffraction pattern having at least the d-spacings and intensities set forth in Table B:

TABLE B

| 2θ | d (Å) | I/Io % |
|---|---|---|
| 7.45-7.72 | 11.86-11.44 | m-s |
| 9.35-9.53 | 9.45-9.27 | m-s |
| 12.30-13.00 | 7.19-6.80 | m-s |
| 13.25-13.73 | 6.68-6.44 | m-s |
| 15.20-15.80 | 5.82-5.60 | w-m |
| 21.06-21.62 | 4.22-4.11 | m |
| 22.16-22.62 | 4.01-3.93 | m-vs |
| 23.73-24.06 | 3.75-3.70 | m |
| 25.15-25.44 | 3.54-3.50 | vs |
| 25.51-25.95 | 3.49-3.43 | m-vs |
| 28.40-28.57 | 3.14-3.12 | m |
| 30.55-31.15 | 2.92-2.87 | m |
| 49.70-50.40 | 1.83-1.81 | w-m |

Yet another embodiment of the invention is a hydrocarbon conversion process comprising contacting a hydrocarbon stream with a crystalline microporous zeolitic composition at hydrocarbon conversion conditions to give a converted product, the crystalline microporous zeolitic composition having a three-dimensional framework composed of at least tetrahedral $SiO_2$ units and an empirical composition on an anhydrous basis expressed by the empirical formula of:

$$M1_m^{n+}Al_{1-x}E_xSi_yO_z$$

where M1 is at least one exchangeable cation selected from the group consisting of protons, alkali, alkaline earth, transition metals, and rare earth metals, "m" is the mole ratio of M1 to (Al+E) and varies from 0.05 to about 10.0, "n" is the weighted average valence of M1 and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation:

$$z=(m\cdot n+3+4\cdot y)/2$$

and is characterized in that it has an x-ray diffraction pattern having at least the d-spacings and intensities set forth in Table D:

TABLE D

| 2θ | d (Å) | I/Io % |
|---|---|---|
| 9.20-9.70 | 9.60-9.11 | m |
| 12.45-12.85 | 7.10-6.88 | m-vs |
| 13.40-13.65 | 6.60-6.48 | m-s |
| 14.10-14.40 | 6.28-6.15 | w-m |
| 22.40-22.65 | 3.97-3.92 | m-vs |
| 23.85-24.10 | 3.73-3.69 | w-m |
| 25.22-25.45 | 3.53-3.50 | vs |
| 25.89-26.10 | 3.44-3.41 | m |

These and other objects and embodiments of the invention will become more apparent after the detailed description of the invention.

DETAILED DESCRIPTION OF THE INVENTION

Applicants have prepared the a series of crystalline aluminosilicate compositions designated the UZM-26 family of compositions which include the as synthesized composition, UZM-26P, a calcined composition, UZM-26, an ion-exchanged composition, UZM-26PX, and an ion-exchanged version calcined composition, UZM-26X. Each of these species has a unique topology/structure. While UZM-26P and UZM-26PX are layered compositions, the calcined products, UZM-26 and UZM-26X are microporous three dimensional zeolites. UZM-26P has an empirical composition in the as-synthesized form and on an anhydrous basis expressed by the empirical formula:

$$M_m^{n+}R_r^{p+}Al_{1-x}E_xSi_yO_z$$

where M is at least one exchangeable cation and is selected from the group consisting of alkali metal ions, alkaline earth metal ions, and rare earth metal ions. Specific examples of the M cations include but are not limited to lithium, sodium, potassium, rubidium, cesium, calcium, strontium, barium, lanthanum, ytterbium and mixtures thereof, with calcium being preferred. R is an organoammonium cation or an amine, examples of which include but are not limited to the hexyltrimethylammonium cation, choline cation $[(CH_3)_3NCH_2CH_2OH]^+$, ethyltrimethylammonium, diethyldimethylammonium, trimethylpropylammonium, trimethylbutylammonium, trimethylpentylammonium, dimethyldiethanolammonium, tetraethylammonium (TEA$^+$), tetrapropylammonium TPA$^+$, dimethylhexylamine, diethanolamine and mixtures thereof and "r" is the mole ratio of R to (Al+E) and varies from about 0.5 to about 10.0. Hexyltrimethylammonium is a preferred organoammonium cation. The value of "p" which is the weighted average valence of R varies from 1 to about 2. The value of "n" which is the weighted average valence of M varies from about 1 to about 3 while "m" is the mole ratio of M to (Al+E) and varies from 0.05 to about 10. The ratio of silicon to (Al+E) is represented by "y" which varies from about 5 to about 40. E is an element which is tetrahedrally coordinated, is present in the framework and is selected from the group consisting of gallium, iron and boron. The mole fraction of E is represented by "x" and has a value from 0 to about 1.0, while "z" is the mole ratio of 0 to (Al+E) and is given by the equation:

$$z=(m·n+p·r+3+4·y)/2.$$

When M is only one metal, then the weighted average valence is the valence of that one metal, i.e. +1 or +2.

However, when more than one M metal is present, the total amount of:

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

When more than one organoammonium cation or amine is present, the total amount of $$R_r^{p+}=R_{r1}^{(p1)+}+R_{r2}^{(p2)+}+R_{r3}^{(p3)+}+\ldots.$$

And the weighted average valence "p" is given by the equation:

$$p = \frac{r_1 \cdot p_1 + r_2 \cdot p_2 + r_3 \cdot p_3 + \ldots}{r_1 + r_2 + r_3 \ldots}$$

UZM-26P, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals include the halide salts, nitrate salts, acetate salts, and hydroxides of the respective alkali, alkaline earth, or rare earth metals. R is an organoammonium cation or an amine selected from the group consisting of hexyltrimethylammonium, pentyltrimethylammonium, choline, ethyltrimethylammonium, diethyldimethylammonium, TEA, TPA, trimethylpropylammonium, trimethylbutylammonium, dimethyldiethanolammonium, dimethylhexylamine, diethanolamine and mixtures thereof, and the sources include the hydroxide, chloride, bromide, iodide and fluoride compounds. Specific examples include without limitation hexyltrimethylammonium hydroxide and hexyltrimethylammonium chloride, pentyltrimethylammonium hydroxide, ethyltrimethylammonium hydroxide, diethyldimethylammonium hydroxide, tetraethylammonium hydroxide, tetrapropylammonium hydroxide, tetrapropylammonium chloride.

The reaction mixture containing reactive sources of the desired components can be described in terms of molar ratios of the oxides by the formula:

$$aM_{2/n}O:bR_{2/p}O:1-cAl_2O_3:cE_2O_3:dSiO_2:eH_2O$$

where "a" varies from about 0.05 to about 10.0, "b" varies from about 2.5 to about 120, "c" varies from 0 to 1.0, "d" varies from about 10 to about 150, and "e" varies from about 25 to about 6000. If alkoxides are used, it is preferred to include a distillation or evaporative step to remove the alcohol hydrolysis products. The reaction mixture is now reacted at a temperature of about 60° C. to about 175° C. and preferably from about 100° C. to about 150° C. for a period of about 1 day to about 3 weeks and preferably for a time of about 6 days to about 15 days in a sealed reaction vessel under autogenous pressure. After crystallization is complete, the solid product is isolated from the reaction mixture by means such as filtration or centrifugation, and then washed with deionized water and dried in air at ambient temperature up to about 100° C. A preferred synthetic approach to make UZM-26P utilizes the charge density mismatch process disclosed in US Patent Application Publication No. US 2005/0095195 which is incorporated by reference in its entirety. The charge density mismatch process allows multiple structure directing agents to cooperate to crystallize a single structure. The method employs appropriate quaternary ammonium hydroxides to solubilize aluminosilicate species, creating a reaction mixture which has difficulty crystallizing and condensing to form a solid under synthesis conditions. These preformed aluminosilicate species require crystallization-inducing agents such as alkali and alkaline earth metals or more highly charged organoammonium cations that are separately introduced and cooperate with the quaternary ammonium template to affect the crystallization process. A preferred combination for the synthesis of UZM-26P is hexyltrimethylammonium hydroxide as the charge density mismatch template and calcium as the crystallization inducing agent.

The UZM-26P crystalline layered aluminosilicate, which is obtained from the above-described process, is characterized by an x-ray diffraction pattern having at least the d-spacings and relative intensities set forth in Table A below.

TABLE A

| 2θ | d (Å) | I/Io % |
|---|---|---|
| 5.32-5.88 | 16.60-15.02 | m-vs |
| 8.10-8.94 | 10.91-9.89 | w-m |
| 12.40-12.75 | 7.13-6.94 | w-m |
| 13.15-13.65 | 6.73-6.48 | m |
| 21.10-21.55 | 4.21-4.12 | m |
| 22.00-22.40 | 4.04-3.97 | m |
| 23.55-23.88 | 3.78-3.72 | w-m |
| 24.95-25.31 | 3.57-3.52 | m-vs |
| 25.47-25.88 | 3.49-3.44 | m |
| 28.06-28.44 | 3.18-3.14 | w-m |
| 49.78-50.28 | 1.83-1.81 | m |

UZM-26P is a layered composition and can be converted to a microporous crystalline three-dimensional aluminosilicate zeolite, UZM-26, by calcination. The condensation of the layers to form the microporous three-dimensional UZM-26 occurs at calcination temperatures greater than 400° C. and preferably at temperatures greater than 500° C. for times sufficient to decompose and remove the organoammonium template and effect condensation. The time can vary considerably but is usually from about 3 hr to about 24 hr. The resulting UZM-26 is characterized by a three-dimensional framework composed of at least tetrahedral SiO$_2$ units and an empirical composition on an anhydrous basis expressed by the empirical formula of:

$$M_m^{n+}Al_{1-x}E_xSi_yO_z$$

where M is at least one exchangeable cation selected from the group consisting of hydrogen ion, alkali, alkaline earth, and rare earth metals, "m" is the mole ratio of M to (Al+E) and varies from 0.05 to about 10.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation:

$$z=(m\cdot n+3+4\cdot y)/2$$

Where M is only one metal, then the weighted average valence is the valence of that one metal, i.e. +1 or +2.

However, when more than one M metal is present, the total amount of:

$$M_m^{n+}=M_{m1}^{(n1)+}+M_{m2}^{(n2)+}+M_{m3}^{(n3)+}+\ldots$$

and the weighted average valence "n" is given by the equation:

$$n=\frac{m_1\cdot n_1+m_2\cdot n_2+m_3\cdot n_3+\ldots}{m_1+m_2+m_3\ldots}$$

and is characterized in that it has the x-ray diffraction pattern having at least the d-spacings and intensities set forth in Table B:

TABLE B

| 2θ | d (Å) | I/Io % |
|---|---|---|
| 7.45-7.72 | 11.86-11.44 | m-s |
| 9.35-9.53 | 9.45-9.27 | m-s |
| 12.30-13.00 | 7.19-6.80 | m-s |
| 13.25-13.73 | 6.68-6.44 | m-s |
| 15.20-15.80 | 5.82-5.60 | w-m |
| 21.06-21.62 | 4.22-4.11 | m |
| 22.16-22.62 | 4.01-3.93 | m-vs |
| 23.73-24.06 | 3.75-3.70 | m |
| 25.15-25.44 | 3.54-3.50 | vs |
| 25.51-25.95 | 3.49-3.43 | m-vs |
| 28.40-28.57 | 3.14-3.12 | m |
| 30.55-31.15 | 2.92-2.87 | m |
| 49.70-50.40 | 1.83-1.81 | w-m |

The UZM-26P aluminosilicate may also be ion-exchanged with hydrogen ion, ammonium ion, alkali, alkaline earth, transition metal, or rare earth metal cations to form a new category of layered compositions with a distinct x-ray pattern designated UZM-26PX. The new structure results from a rearrangement of the layers with respect to each other as some or all of the organoammonium template and Ca are removed from UZM-26P during the ion-exchange process. UZM-26PX layers are composed of at least tetrahedral SiO$_2$ units and an empirical composition on an anhydrous basis expressed by the empirical formula of:

$$M'_m{}^{n+}R_r{}^{p+}Al_{1-x}E_xSi_yO_z$$

where M is at least one exchangeable cation selected from the group consisting of hydrogen ion, ammonium ion, alkali metal ions, alkaline earth metal ions, transition metal ions and rare earth metal ions. Specific examples of the M cations include but are not limited to lithium, sodium, potassium, rubidium, cesium, calcium, strontium, barium, zinc, iron, copper, manganese, lanthanum, ytterbium and mixtures thereof. R is an organoammonium cation or an amine examples of which are selected from the group consisting of hexyltrimethylammonium (HTMA$^+$), hexamethonium, pentyltrimethylammonium, choline, ethyltrimethylammonium (ETMA$^+$), diethyldimethylammonium (DEDMA$^+$), trimethylpropylammonium, trimethylbutylammonium, dimethyldiethanolammonium, tetraethylammonium (TEA$^+$), tetrapropylammonium (TPA$^+$), dimethylhexylamine, diethanolamine and mixtures thereof, "r" is the mole ratio of R to (Al+E) and has a value of about 0.01 to about 10.0. The value of "m" is the mole ratio of M to (Al+E) and varies from 0.01 to about 10.0, "n" is the weighted average valence of M and has a value of about 1 to about 3, "p" is the weighted average valence of R and has a value of about 1 to about 2, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation:

$$z=(m \cdot n+p \cdot r+3+4 \cdot y)/2$$

When M' is only one cation, then the weighted average valence is the valence of that one cation, i.e. +1 or +2. However, when more than one M' metal is present, the total amount of:

$$M'^{n+}_m = M'^{(n1)+}_{m1} + M'^{(n2)+}_{m2} + M'^{(n3)+}_{m3} + \ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

And when more than one R' organoammonium cation or amine is present, the total amount of:

$$R'^{p+}_r = R'^{(p1)+}_{r1} + R'^{(p2)+}_{r2} + R'^{(p3)+}_{r3} + \ldots$$

and the weighted average valence "p" is given by the equation:

$$p = \frac{r_1 \cdot p_1 + r_2 \cdot p_2 + r_3 \cdot p_3 + \ldots}{r_1 + r_2 + r_3 \ldots}$$

and is characterized in that it has an x-ray diffraction pattern having at least the d-spacings and intensities set forth in Table C:

TABLE C

| 2θ | d (Å) | I/Io % |
|---|---|---|
| 8.27-9.13 | 10.68-9.68 | m |
| 12.45-12.82 | 7.10-6.90 | m |
| 13.33-13.61 | 6.64-6.50 | m |
| 22.21-22.48 | 4.00-3.95 | m |
| 23.74-24.05 | 3.74-3.70 | m |
| 24.33-24.58 | 3.66-3.62 | m |
| 25.20-25.42 | 3.53-3.50 | vs |
| 28.22-28.75 | 3.16-3.10 | w-m |
| 48.62-48.97 | 1.87-1.86 | w-m |
| 65.15-65.90 | 1.43-1.42 | w |

The ion-exchange of UZM-26P to form UZM-26PX is carried out by stirring UZM-26P suspended in a solution containing an excess of the exchange cation. The exchange is usually carried out for a period of 2-24 hours at temperatures ranging from 15° C. to 95° C. The product is isolated by filtration or centrifugation and is washed with deionized water. This process may be carried out as many times as necessary to achieve the exchange of cations.

Another embodiment of the UZM-26 family of crystalline aluminosilicate compositions is derived from the ion-exchange of UZM-26P with an organoammonium cation different from the starting organoammonium cation. As such, the layers may be "expanded" or exfoliated with appropriate organoammonium salts such as cetyltrimethylammonium. These compositions are highly variable with respect to an x-ray diffraction pattern, but several are included here in the examples. Such expanded compositions may also be further exchanged with pillaring agents, such as $[Al_{13}O_4(OH)_{24}(H_2O)_{12}]^{7+}$ or $[Zr_4(OH)_8(H_2O)_{16}]^{8+}$ to make new microporous compositions.

The exchanged aluminosilicate, UZM-26PX, is a layered composition and can be converted to UZM-26X, a microporous aluminosilicate zeolite by calcination. The condensation of the layers to form the microporous UZM-26X occurs at calcination temperatures greater than 400° C. and preferably at temperatures greater than 500° C. for times sufficient to decompose and remove the organoammonium template and effect condensation. Although the amount of time can vary considerably, typically the amount of time varies from about 2 hr to about 24 hr. The resulting UZM-26X consists of a three-dimensional framework composed of at least tetrahedral $SiO_2$ units and has an empirical composition on an anhydrous basis expressed by an empirical formula of:

$$M1_m^{n+}Al_{1-x}E_xSi_yO_z$$

where M1 is at least one exchangeable cation selected from the group consisting of hydrogen ion, alkali metal ions, alkaline earth metal ions, transition metal ions, and rare earth metal ions, "m" is the mole ratio of M1 to (Al+E) and varies from 0.05 to about 10.0, "n" is the weighted average valence of M1 and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation:

$$z=(m \cdot n+3+4 \cdot y)/2$$

When M1 is only one cation, then the weighted average valence is the valence of that one cation, i.e. +1 or +2. However, when more than one M1 metal is present, the total amount of:

$$M1_m^{n+} = M1_{m1}^{(n1)+} + M1_{m2}^{(n2)+} + M1_{m3}^{(n3)+} + \ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

and is characterized in that it has the x-ray diffraction pattern having at least the d-spacings and intensities set forth in Table D:

TABLE D

| 2θ | d (Å) | I/Io % |
|---|---|---|
| 9.20-9.70 | 9.60-9.11 | m |
| 12.45-12.85 | 7.10-6.88 | m-vs |
| 13.40-13.65 | 6.60-6.48 | m-s |
| 14.10-14.40 | 6.28-6.15 | w-m |
| 22.40-22.65 | 3.97-3.92 | m-vs |
| 23.85-24.10 | 3.73-3.69 | w-m |
| 25.22-25.45 | 3.53-3.50 | vs |
| 25.89-26.10 | 3.44-3.41 | m |

The microporous UZM-26 and UZM-26X compositions will contain some of the exchangeable or charge balancing cations in its pores. These exchangeable cations can be exchanged for other cations. The UZM-26 and UZM-26X zeolites may be modified in many ways to tailor them for use in a particular application. Modifications include calcination, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that can be modified include porosity, adsorption, Si/Al ratio, acidity, thermal stability, etc.

The UZM-26 and UZM-26X compositions which are modified by one or more techniques described in the '975 patent (herein UZM-26HS and UZM-26X HS) are described by the empirical formula on an anhydrous basis of:

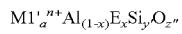

$$M1'^{n+}_{a}Al_{(1-x)}E_xSi_{y'}O_{z''}$$

where M1' is at least one exchangeable cation selected from the group consisting of alkali, alkaline earth metals, transitions metals, rare earth metals, ammonium ion, hydrogen ion and mixtures thereof, "a" is the mole ratio of M1' to (Al+E) and varies from about 0.01 to about 50, "n" is the weighted average valence of M1' and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than 8 to virtually pure silica and z' is the mole ratio of 0 to (Al+E) and has a value determined by the equation:

$$z'=(a \cdot n+3+4 \cdot y')/2$$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 8 to 3,000 preferably greater than 20 to about 3,000; 8 to 10,000 preferably greater than 20 to about 10,000 and 8 to 20,000 preferably greater than 20 to about 20,000.

In specifying the proportions of the zeolite starting composition or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-26 and UZM-26X zeolites of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-26 and UZM-26X zeolites of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. No. 4,310,440 and U.S. Pat. No. 4,440,871 which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379–20,685 kPa g). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 1,000 to 50,000 standard cubic feet (scf) per barrel of charge (178-8,888 std. m$^3$/m$^3$), preferably between 2,000 and 30,000 scf per barrel of charge (355-5,333 std. m$^3$/m$^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-26 and UZM-26X compositions using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 hr, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of –30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The following examples are presented in illustration of this invention and are not intended as undue limitations on the generally broad scope of the invention as set out in the appended claims.

The structures of the UZM-26 family of aluminosilicate compositions of this invention were determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 70° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline compositions from each other and from the compositions of the prior art. In some of the x-ray patterns reported, the relative intensities of the d-spacings are indicated by the notations vs, s, m, and w which represent very strong, strong, medium, and weak, respectively. In terms of 100×I/I$_o$, the above designations are defined as:

w=0-15; m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present. Finally, some peaks are identified with special identifiers as follows: very broad (vbr); broad (br); and shoulder (sh).

In order to more fully illustrate the invention, the following examples are set forth. It is to be understood that the examples are only by way of illustration and are not intended as an undue limitation on the broad scope of the invention as set forth in the appended claims.

Example 1

Hexyltrimethylammonium Hydroxide Solution

Hexyltrimethylammonium bromide, (99%) 1488.9 g, was dissolved in 2368.9 g deionized water in a 5 liter 3-necked round bottom flask equipped with overhead stirring. A 1 wt. % excess of Silver(I) oxide, (99%), 761.6 g, was added and stirred in the dark for 44 hours. The resulting hexyltrimethylammonium hydroxide solution was isolated by filtration.

Standardization of the hexyltrimethylammoniun hydroxide solution via titration with potassium acid phthalate to a phenolphthalein endpoint revealed the solution to be 30.03 wt. % hexyltrimethylammonium hydroxide.

Example 2

Hexyltrimethylammonium Aluminosilicate Solution

Hexyltrimethylammonium hydroxide, (30.03%), 455.04 g, was diluted with 96.72 g deionized water while stirring. Aluminum tri sec-butoxide, (97%), 115.86 g, was added to the solution, which was then cooled in ice prior to the addition of tetraethylorthosilicate, (98%), 200.0 g with stirring. After hydrolysis was complete, the solution was transferred to a rotary evaporator to remove alcohol. A total of 163.7 g. of liquid was removed. Elemental analysis showed the solution to contain 3.74 wt. % Si and 1.77 wt. % Al.

Example 3

Hexyltrimethylammonium Silicate Solution

Hexyltrimethylammonium hydroxide, (30.03%), 492.96 g, was diluted with 1073.86 g deionized water and to it there were added 650.0 g of tetraethylorthosilicate, (98%) with stirring. After hydrolysis was complete, the solution was placed on a rotary evaporator to remove the alcohol. A total of 518.6 g of liquid was removed, after which 150 g of deionized water was added. Elemental analysis showed the solution to contain 5.10 wt % Si.

Example 4

A mixture was formed by adding 57.81 g of hexyltrimethylammonium silicate solution (Example 3), 10.02 g of hexyltrimethylammonium aluminosilicate solution (Example 2), and 34.19 g of hexyltrimethylammonium hydroxide (30.03%) to a beaker with stirring. This was followed by the dropwise addition of 11.56 g of a calcium acetate solution $(Ca(OAc)_2*40\ H_2O)$, accompanied by vigorous stirring. Upon completion of the calcium acetate addition, the resulting mixture was stirred for an additional hour and the reaction mixture was then divided equally among four 45 ml Teflon®-lined autoclaves. The reaction mixtures were reacted at 150° C. for 10, 14, 17, and 21 days respectively.

The solid product from each autoclave was recovered by filtration, washed with de-ionized water and dried at 95° C. The products obtained from all the reactions were identified to be UZM-26P by x-ray diffraction (XRD) analysis. Representative diffraction lines for the product isolated after 14 days are given below in Table 1. Elemental analysis showed the product to consist of elements with the following mole ratios: Si/Al=13.51, Ca/Al=1.81, N/Al=1.37, and C/N=5.90.

TABLE 1

| 2-Θ | d(Å) | I/I$_0$ % | peaks |
|---|---|---|---|
| 5.78 | 15.28 | m | |
| 8.00 | 11.04 | w | sh |
| 8.80 | 10.04 | m | vbr |
| 12.66 | 6.99 | m | |
| 13.50 | 6.55 | m | |
| 17.87 | 4.96 | w | |
| 21.46 | 4.14 | m | sh |
| 22.30 | 3.98 | m | |
| 23.39 | 3.80 | m | |
| 23.76 | 3.74 | m | |
| 25.24 | 3.53 | vs | |
| 25.76 | 3.46 | m | sh |
| 26.99 | 3.30 | w | |
| 28.36 | 3.14 | m | |
| 29.19 | 3.06 | m | |
| 30.94 | 2.89 | m | |
| 45.40 | 2.00 | w | |
| 50.18 | 1.82 | m | |

Example 5

A mixture was formed by adding 60.77 g of hexyltrimethylammonium silicate solution (Example 3), 7.32 g of hexyltrimethylammonium aluminosilicate solution (Example 2), and 34.93 g of hexyltrimethylammonium hydroxide (30.03%) to a beaker with stirring. To the resulting mixture 10.56 g of calcium acetate solution $(Ca(OAc)_2*40\ H_2O)$, were added dropwise with vigorous stirring. Upon completion of the calcium acetate addition, the resulting mixture was stirred for an additional hour and then was divided equally among four 45 ml Teflon®-lined autoclaves. The mixtures were reacted at 150° C. for 10, 14, 17, and 21 days respectively.

The solid product from each autoclave was recovered by filtration, washed with de-ionized water and dried at 95° C. The products obtained from all the reactions were identified to be UZM-26P by XRD analysis. Representative diffraction lines for the 10-day and the 21-day product are shown in Table 2 below. Elemental analysis showed the products to consist of elements with the following mole ratios:

10-day product: Si/Al=15.46, Ca/Al=2.13, N/Al=1.96, and C/N=5.49;

21-day product: Si/Al=16.67, Ca/Al=2.14, N/Al=1.84, and C/N=6.09.

TABLE 2

| | 10-day product | | | | 21-day product | | |
|---|---|---|---|---|---|---|---|
| 2-Θ | d(Å) | I/I₀% | peaks | 2-Θ | d(Å) | I/I₀% | peaks |
| 5.42 | 16.29 | vs | | 5.44 | 16.23 | vs | |
| 8.24 | 10.72 | m | vbr | 7.82 | 11.30 | w | sh |
| 12.48 | 7.09 | m | | 8.30 | 10.65 | m | vbr |
| 13.30 | 6.65 | m | | 12.48 | 7.09 | m | |
| 21.30 | 4.17 | m | | 13.28 | 6.66 | m | |
| 22.24 | 3.99 | m | | 21.22 | 4.18 | m | |
| 23.06 | 3.85 | m | | 22.14 | 4.01 | m | |
| 23.64 | 3.76 | m | | 22.82 | 3.89 | m | |
| 25.06 | 3.55 | s | | 23.64 | 3.76 | m | |
| 25.79 | 3.45 | m | sh | 25.02 | 3.56 | vs | |
| 28.14 | 3.17 | m | | 25.60 | 3.48 | m | sh |
| 28.48 | 3.13 | w | | 28.18 | 3.16 | m | |
| 28.94 | 3.08 | m | | 28.63 | 3.11 | m | |
| 29.28 | 3.05 | m | | 30.52 | 2.93 | w | |
| 30.65 | 2.91 | m | | 49.88 | 1.83 | m | |
| 48.61 | 1.87 | w | | | | | |
| 49.90 | 1.83 | m | | | | | |
| 65.35 | 1.43 | w | | | | | |

Example 6

A mixture was formed by adding 65.03 g of hexyltrimethylammonium silicate solution (Example 3), 4.74 g of hexyltrimethylammonium aluminosilicate solution (Example 2), and 33.06 g of hexyltrimethylammonium hydroxide (30.03%) to a beaker with stirring. To the resulting mixture 10.93 g of calcium acetate solution (Ca(OAc)$_2$*40 H$_2$O), were added dropwise with vigorous stirring. Upon completion of the calcium acetate addition, the resulting mixture was stirred for an additional hour and then was divided equally among four 45 ml Teflon®-lined autoclaves, which were reacted at 150° C. for 10, 14, 17, and 21 days respectively.

The solid product from each autoclave was recovered by filtration, washed with de-ionized water and dried at 95° C. The products obtained from all the reactions were identified to be UZM-26P by XRD analysis. Representative diffraction lines for the 14-day and the 21-day product are shown in Table 3 below. Elemental analysis showed the products to consist of elements with the following mole ratios:
14-day product: Si/Al=21.25, Ca/Al=3.51, N/Al=2.46, and C/N=6.42;
21-day product: Si/Al=23.14, Ca/Al=3.52, N/Al=2.42, and C/N=5.83.

TABLE 3

| | 14-day product | | | | 21-day product | | |
|---|---|---|---|---|---|---|---|
| 2-Θ | d(Å) | I/I₀% | peaks | 2-Θ | d(Å) | I/I₀% | peaks |
| 5.46 | 16.18 | vs | | 5.44 | 16.23 | vs | |
| 7.86 | 11.25 | w | sh | 8.52 | 10.37 | m | br |
| 8.56 | 10.32 | w | br | 12.52 | 7.07 | m | |
| 12.50 | 7.08 | w | | 13.24 | 6.68 | m | |
| 13.32 | 6.64 | m | | 21.26 | 4.18 | m | |
| 21.20 | 4.19 | m | | 22.09 | 4.02 | m | |
| 22.20 | 4.00 | m | | 22.84 | 3.89 | m | |
| 23.70 | 3.75 | m | | 23.68 | 3.75 | m | |
| 25.16 | 3.54 | m | | 25.02 | 3.56 | s | |
| 25.56 | 3.48 | m | sh | 25.66 | 3.47 | m | sh |
| 28.24 | 3.16 | w | | 28.16 | 3.17 | m | |
| 28.56 | 3.12 | m | | 29.19 | 3.06 | w | |
| 29.02 | 3.07 | m | | 30.78 | 2.90 | m | |
| 29.35 | 3.04 | w | | 49.90 | 1.83 | m | |
| 30.62 | 2.92 | w | | | | | |
| 37.46 | 2.40 | w | | | | | |
| 49.96 | 1.82 | m | | | | | |

Example 7

An aluminosilicate reaction mixture was prepared by first dissolving 1.58 g of aluminum tri sec-butoxide (95⁺%) in 77.39 g of hexyltrimethylammonium hydroxide, (30.03%), with vigorous stirring. To this mixture, colloidal silica (Ludox AS-40, 40% SiO$_2$), 23.90 g, was added. The reaction mixture was mixed for 1 hour at which point 14.06 g of a calcium acetate solution, (Ca(OAc)$_2$*40H$_2$O), was added dropwise. The resultant reaction mixture was homogenized for an additional hour and then divided equally between two 125 cc Teflon®-lined autoclaves and reacted at 150° C. for 14 days.

The solid product from each autoclave was recovered by filtration, washed with de-ionized water and dried at 95° C. The product obtained from both autoclaves was identified to be UZM-26P by XRD analysis. Representative diffraction lines for the product from one of the autoclaves are shown in Table 4 below. Elemental analysis showed the product to consist of elements with the following mole ratios: Si/Al=16.79, Ca/Al=2.25, N/Al=1.42, and C/N=7.07.

TABLE 4

| 2-Θ | d(Å) | I/I₀% | peaks |
|---|---|---|---|
| 5.52 | 16.00 | vs | |
| 8.80 | 10.04 | m | br |
| 12.54 | 7.05 | m | |
| 13.42 | 6.59 | m | |
| 21.40 | 4.15 | m | |
| 22.34 | 3.98 | m | |
| 23.18 | 3.83 | m | |
| 23.73 | 3.75 | m | |
| 25.22 | 3.53 | s | |
| 25.68 | 3.47 | m | sh |
| 26.92 | 3.31 | m | |
| 28.12 | 3.17 | w | |
| 28.30 | 3.15 | m | |
| 28.64 | 3.11 | m | |
| 29.01 | 3.08 | w | |
| 30.51 | 2.93 | m | |
| 48.72 | 1.87 | w | |
| 50.16 | 1.82 | m | |

Example 8

This example details the synthesis of the UZM-26P composition which was ion-exchanged in the subsequent examples. An aluminosilicate reaction mixture was prepared by first dissolving 12.64 g of aluminum sec-butoxide (95⁺%) in 619.12 g of hexyltrimethylammonium hydroxide (30.03%) with vigorous stirring. This was followed by the addition of colloidal silica (Ludox AS-40, 40% SiO$_2$), 191.2 g, The resulting reaction mixture was homogenized for 1 hour Then there were added 112.48 g of a calcium acetate solution (Ca(OAc)$_2$*40H$_2$O) dropwise with stirring. The reaction mixture was mixed for an additional hour and then loaded into a 2 liter static autoclave and reacted for 13 days at 150° C.

The solid product was recovered by filtration, washed with de-ionized water and dried at 95° C. The resulting product was identified to be UZM-26P by XRD analysis. Representative diffraction lines for the product are shown in Table 5 below. Elemental analysis showed the composition of the product to consist of the following mole ratios: Si/Al=17.10, Ca/Al=2.45, N/Al=1.90, and C/N=6.86.

TABLE 5

| 2-Θ | d(Å) | I/I₀% | peaks |
|---|---|---|---|
| 5.52 | 16.00 | vs | |
| 8.52 | 10.37 | m | br |
| 12.64 | 7.00 | m | |
| 13.48 | 6.57 | m | |
| 14.06 | 6.29 | w | |
| 21.28 | 4.17 | m | |
| 22.26 | 3.99 | m | |
| 23.80 | 3.74 | w | |
| 24.41 | 3.64 | m | |
| 25.18 | 3.53 | s | |
| 25.58 | 3.48 | m | sh |
| 25.96 | 3.43 | m | |
| 28.34 | 3.15 | m | |
| 49.98 | 1.82 | m | |
| 66.08 | 1.41 | w | |

Examples 9-14

UZM-26 compositions are crystalline microporous zeolites derived from the calcination of the as-synthesized UZM-26P precursors. Examples 9-14 present the synthesis of UZM-26 from UZM-26P at various conditions. The results from these examples are presented in Table 6 along with surface area analysis results. The calcination was carried out under a flow of dry air, ramping first at 1° C./min to 350° C., holding for an hour, ramping at 1° C./min to the calcination temperature indicated in Table 6 and holding at that temperature for the amount of time indicated. After calcination, the materials were characterized by XRD analysis. The representative diffraction lines for each UZM-26 composition are shown in Tables 7-10. The BET method was used to obtain the surface area data.

TABLE 6

| Example | Parent UZM-26P | Calcination Conditions | Surface Area; Micropore Volume (BET) | Diffraction Table |
|---|---|---|---|---|
| 9 | Example 4 | 525° C., dry air, 6 hr | 307 m2/g; 0.085 cc/g | Table 7 |
| 10 | Example 5, 10 day | 540° C., dry air, 14 hr | 244 m2/g; 0.066 cc/g | Table 8 |
| 11 | Example 5, 21 day | 525°, dry air, 6 hr | none | Table 8 |
| 12 | Example 6, 21 day | 525° C., dry air, 4 hr | 252 m2/g; 0.061 cc/g | Table 9 |
| 13 | Example 7 | 525° C., dry air, 4 hr | 269 m2/g; 0.067 cc/g | Table 10 |
| 14 | Example 8 | 525° C., dry air, 6 hr | 209 m2/g; 0.057 cc/g | Table 10 |

TABLE 7

Example 9

| 2-Θ | d(Å) | I/I₀% | peaks |
|---|---|---|---|
| 7.53 | 11.74 | m | |
| 9.44 | 9.36 | m | br |
| 12.66 | 6.99 | m | |
| 13.44 | 6.58 | m | |
| 15.71 | 5.64 | w | br |
| 21.28 | 4.17 | m | |
| 22.30 | 3.98 | m | |
| 23.94 | 3.71 | m | |
| 25.30 | 3.52 | vs | |
| 25.70 | 3.46 | m | sh |
| 28.51 | 3.13 | m | |
| 30.82 | 2.90 | m | |
| 49.94 | 1.82 | w | |

TABLE 8

| Example 10 | | | | Example 11 | | | |
|---|---|---|---|---|---|---|---|
| 2-Θ | d(Å) | I/I₀% | peaks | 2-Θ | d(Å) | I/I₀% | peaks |
| 7.66 | 11.53 | m | | 7.52 | 11.75 | m | |
| 9.44 | 9.36 | m | br | 9.40 | 9.40 | m | br |
| 12.58 | 7.03 | s | | 12.42 | 7.12 | s | |
| 13.40 | 6.60 | m | | 13.36 | 6.62 | m | |
| 15.30 | 5.79 | m | | 15.60 | 5.68 | w | br |
| 21.17 | 4.19 | m | | 21.16 | 4.19 | m | |
| 22.40 | 3.97 | m | br | 22.26 | 3.99 | s | |
| 23.90 | 3.72 | m | | 23.84 | 3.73 | m | |
| 25.28 | 3.52 | vs | | 25.24 | 3.53 | vs | |
| 25.70 | 3.46 | m | sh | 25.62 | 3.47 | m | sh |
| 28.54 | 3.13 | m | | 28.32 | 3.15 | m | |
| 30.77 | 2.90 | m | | 30.82 | 2.90 | m | |
| 49.82 | 1.83 | m | | 49.95 | 1.82 | m | |

TABLE 9

Example 12

| 2-Θ | d(Å) | I/I₀% | peaks |
|---|---|---|---|
| 7.57 | 11.68 | s | |
| 9.48 | 9.32 | m | br |
| 12.62 | 7.01 | s | |
| 13.43 | 6.59 | m | |
| 15.44 | 5.74 | m | br |
| 21.30 | 4.17 | m | |
| 22.49 | 3.95 | m | br |
| 23.97 | 3.71 | m | |
| 25.36 | 3.51 | vs | |
| 25.80 | 3.45 | m | sh |
| 28.48 | 3.13 | m | |
| 30.76 | 2.90 | m | |
| 49.94 | 1.82 | m | |

TABLE 10

| Example 13 | | | | Example 14 | | | |
|---|---|---|---|---|---|---|---|
| 2-Θ | d(Å) | I/I₀% | peaks | 2-Θ | d(Å) | I/I₀% | peaks |
| 7.62 | 11.59 | m | | 7.65 | 11.55 | m | |
| 9.40 | 9.40 | s | br | 9.40 | 9.40 | m | Br |
| 12.60 | 7.02 | s | | 12.86 | 6.88 | s | |
| 13.50 | 6.56 | m | | 13.62 | 6.50 | s | |
| 15.52 | 5.70 | m | | 15.60 | 5.68 | m | |
| 21.52 | 4.13 | m | | 21.49 | 4.13 | m | |
| 22.36 | 3.97 | m | | 22.52 | 3.95 | vs | |
| 23.96 | 3.71 | m | | 23.82 | 3.73 | m | |
| 25.28 | 3.52 | vs | | 25.30 | 3.52 | vs | |
| 25.76 | 3.46 | s | sh | 25.84 | 3.45 | vs | sh |
| 28.58 | 3.12 | m | | 28.67 | 3.11 | m | |
| 31.06 | 2.88 | m | | 30.66 | 2.91 | m | |
| 49.92 | 1.83 | m | | 50.27 | 1.81 | m | |

Examples 15-18

UZM-26PX compositions were obtained by ion-exchanging UZM-26P compositions. The UZM-26PX compositions are layered compositions distinct from the UZM-26P compositions, due to the removal of much of the Ca, or other initial metal cation and the organic template during the exchange process. The altered arrangement of aluminosilicate layers leads to a distinct x-ray diffraction pattern for these compositions.

Example 15

The as-synthesized UZM-26P product from example 8 was exchanged with $NH_4Cl$ by suspending 10 g of the UZM-26P powder in 500 g 0.5 M N Cl solution at 75° C. for an hour with stirring. After an hour, the exchanged product was isolated by filtration and washed with deionized water. The process was repeated four times. The solid product was dried at 95° C. and identified to be UZM-26PX by XRD analysis. Representative diffraction lines for the product are shown in Table 11 below. Elemental analysis showed the composition of the product to consist of the following mole ratios: Si/Al=15.56, Ca/Al=0.03, N/Al=1.11, and C/N=4.43.

TABLE 11

| 2-Θ | d(Å) | I/I$_0$ % |
|---|---|---|
| 8.46 | 10.45 | m |
| 12.56 | 7.04 | m |
| 13.46 | 6.57 | m |
| 22.38 | 3.97 | m |
| 23.84 | 3.73 | m |
| 24.43 | 3.64 | m |
| 25.32 | 3.51 | vs |
| 28.42 | 3.14 | m |
| 48.72 | 1.87 | m |
| 65.31 | 1.43 | w |

Example 16

The ammonium exchanged UZM-26PX material from Example 15 was now exchanged with sodium as follows. Approximately 250 ml of 0.5 M NaCl solution was adjusted to pH 9 with 1 M NaOH solution, to which 2.4 g of the ammonium exchanged UZM-26PX material was added and stirred at room temperature for an hour. The product was isolated by filtration and washed with de-ionized water. The process was repeated three times. The solid product was dried at 95° C. and identified to be UZM-26PX by XRD analysis. Representative diffraction lines for the product are shown in Table 12 below. Elemental analysis showed the composition of the product to consist of the following mole ratios: Si/Al=17.68, Na/Al=0.24, N/Al=0.75, and C/N=5.96.

TABLE 12

| 2-Θ | d(Å) | I/I$_0$ % |
|---|---|---|
| 8.92 | 9.91 | m |
| 12.64 | 7.00 | m |
| 13.48 | 6.56 | m |
| 22.35 | 3.98 | m |
| 23.84 | 3.73 | m |
| 24.44 | 3.64 | m |
| 25.28 | 3.52 | vs |
| 28.58 | 3.12 | m |
| 48.80 | 1.86 | w |
| 65.45 | 1.42 | w |

Example 17

The ammonium exchanged UZM-26PX material from Example 15 was exchanged with calcium as follows. Approximately 250 ml of 0.5 M calcium acetate solution was adjusted to pH 9 with 1 M NaOH solution, to which 2.4 g of the ammonium exchanged UZM-26PX material was added and stirred at room temperature for an hour. The product was isolated by filtration and was washed with de-ionized water. The process was repeated three times. The solid product was dried at 95° C. and identified to be UZM-26PX by XRD analysis. Representative diffraction lines for the product are shown in Table 13 below. Elemental analysis showed the composition of the product to consist of the following mole ratios: Si/Al=15.27, Ca/Al=0.30, N/Al=0.58, and C/N=7.66.

TABLE 13

| 2-Θ | d(Å) | I/I$_0$ % |
|---|---|---|
| 8.96 | 9.86 | m |
| 12.72 | 6.96 | m |
| 13.54 | 6.53 | m |
| 22.40 | 3.97 | m |
| 23.98 | 3.71 | m |
| 24.52 | 3.63 | m |
| 25.38 | 3.51 | vs |
| 28.32 | 3.15 | w |
| 48.90 | 1.86 | w |
| 65.46 | 1.42 | w |

Example 18

The ammonium exchanged UZM-26PX material from Example 15 was exchanged with lanthanum as follows. Approximately 250 ml of 0.5 M lanthanum acetate solution was adjusted to pH 7.5 with 1 M NaOH solution, to which 2.4 g of the ammonium exchanged UZM-26PX material was added and stirred at room temperature for an hour. The product was isolated by filtration and washed with de-ionized water. The process was repeated three times. The solid product was dried at 95° C. and was identified to be UZM-26PX by XRD analysis. Representative diffraction lines for the product are shown in Table 14 below. Elemental analysis showed the composition of the product to consist of the following mole ratios: Si/Al=15.55, La/A=0.81, N/A=0.75, and C/N=5.99.

TABLE 14

| 2-Θ | d(Å) | I/I$_0$ % |
|---|---|---|
| 8.58 | 10.30 | m |
| 12.56 | 7.04 | m |
| 13.42 | 6.59 | m |
| 22.30 | 3.98 | m |
| 23.92 | 3.72 | m |
| 24.40 | 3.64 | m |
| 25.26 | 3.52 | vs |
| 28.66 | 3.11 | m |
| 48.70 | 1.87 | w |
| 65.75 | 1.42 | w |

Examples 19 and 20

The layers of UZM-26P or UZM-26PX can also undergo ion-exchange with suitable organic materials vs. the metal, or ammonium ions described above. These compositions can be treated with organoammonium cations to affect the exchange, or alternatively, the ammonium or proton form of UZM-26PX may be treated with an amine to accomplish the exchange. Unlike the metal cations used for exchange, the possible organoammonium and amine species that may be used for these exchanges may vary greatly in size. Often it is said that the layers are "expanded" upon ion-exchanging with rather large organoammonium or amine species that significantly increase the interlayer spacing. Because there are many possible variations, it is difficult to characterize these materials with a single powder x-ray diffraction pattern. These "expanded" compositions may be further treated by ion-exchange with the metal cations mentioned above or pillaring agents, such as $[Al_{13}O_4(OH)_{24}(H_2O)_{12}]^{7+}$, $Zr_4(OH)_8(H_2O)_{16}]^{8+}$, etc., and calcined to make new microporous compositions based on the UZM-26P-type layers.

Example 19

As synthesized UZM-26P, 1 g, was suspended in a solution of 30 ml of cetyltrimethylammonium chloride (25%) diluted with 70 ml of de-ionized water. The suspension was stirred for 24 hr, after which the product was isolated by filtration, washed with de-ionized water, and dried at room temperature. Representative diffraction lines for the "expanded" exchange product are shown in Table 15 below.

TABLE 15

| 2-Θ | d(Å) | I/I₀ % |
|---|---|---|
| 2.24 | 39.47 | vs |
| 4.52 | 19.56 | m |
| 6.82 | 12.95 | w |
| 8.53 | 10.36 | w |
| 12.76 | 6.93 | w |
| 13.48 | 6.57 | w |
| 21.48 | 4.13 | m |
| 22.48 | 3.95 | m |
| 24.41 | 3.64 | w |
| 25.26 | 3.52 | m |
| 26.47 | 3.37 | w |
| 50.19 | 1.82 | m |

Example 20

As synthesized UZM-26P, 1 g, was suspended in a solution of 30 ml of cetyltrimethylammonium chloride (25%) diluted with 70 ml of de-ionized water to which there were added 20 g tetrapropylammonium hydroxide, (40%). The suspension was heated to 95° C. and stirred for 16 hrs after which the time the product was isolated by filtration, washed with de-ionized water, and dried at room temperature. Representative diffraction lines for the resulting "expanded" exchange product are shown in Table 16 below.

TABLE 16

| 2-Θ | d(Å) | I/I₀ % |
|---|---|---|
| 2.20 | 40.21 | vs |
| 4.40 | 20.07 | m |
| 6.67 | 13.23 | w |
| 18.65 | 4.76 | w |
| 21.50 | 4.13 | w |
| 29.93 | 2.98 | w |
| 30.03 | 2.97 | w |
| 50.12 | 1.82 | w |

Examples 19 and 20 are only representative of all the possible ways to expand the layer spacing of the layered compositions of the invention.

Examples 21-24

As stated above, the UZM-26PX compositions, the layered, ion-exchanged version of UZM-26P can be calcined to yield crystalline, microporous zeolites designated UZM-26X. These compositions have a distinct x-ray pattern from those derived from the direct calcination of the UZM-26P compositions, which yield UZM-26. Examples 21-24 present the preparation of various UZM-26X compositions. The results of these experiments are presented in Table 17 which provides data on which UZM-26PX sample was used, the calcination conditions, the surface area data and identifies which table contains the respective x-ray diffraction data. The calcination is carried out under a flow of dry air or nitrogen, ramping first at 1° C./min to 350° C., holding for an hour, ramping at 1° C./min to the calcination temperature indicated in the Table 17 and holding at that temperature for the amount of time indicated. After calcination, the compositions were characterized by XRD analysis. The representative diffraction lines for each UZM-26X composition are shown in Tables 18 and 19. The BET method was used to obtain the surface area data.

TABLE 17

| Example | Parent UZM-26PX | Calcination Conditions | Surface Area; Micropore Volume (BET) | Diffraction Table |
|---|---|---|---|---|
| 21 | Example 15 | 540° C., dry air, 4 hr | 379 m²/g; 0.078 cc/g | Table 18 |
| 22 | Example 16 | 550° C., nitrogen, 6 hr | 356 m²/g; 0.070 cc/g | Table 18 |
| 23 | Example 17 | 550° C., nitrogen, 6 hr | 332 m²/g; 0.066 cc/g | Table 19 |
| 24 | Example 18 | 550° C., nitrogen, 6 hr | 295 m²/g; 0.054 cc/g | Table 19 |

TABLE 18

| Example 21 | | | | Example 22 | | | |
|---|---|---|---|---|---|---|---|
| 2-Θ | d(Å) | I/I₀ % | peaks | 2-Θ | d(Å) | I/I₀ % | peaks |
| 9.60 | 9.20 | m | br | 9.51 | 9.30 | m | br |
| 12.72 | 6.95 | m | | 12.68 | 6.97 | vs | |
| 13.54 | 6.54 | m | | 13.56 | 6.53 | s | |
| 14.21 | 6.23 | m | | 14.30 | 6.19 | m | |
| 22.56 | 3.94 | m | | 22.50 | 3.95 | s | |
| 24.00 | 3.70 | m | | 24.03 | 3.70 | m | |
| 25.30 | 3.52 | vs | | 25.38 | 3.51 | vs | |
| 26.00 | 3.42 | m | sh | 25.98 | 3.43 | s | sh |

TABLE 19

| Example 23 | | | | Example 24 | | | |
|---|---|---|---|---|---|---|---|
| 2-Θ | d(Å) | I/I$_0$ % | peaks | 2-Θ | d(Å) | I/I$_0$ % | peaks |
| 9.30 | 9.50 | m | br | 9.61 | 9.20 | m | br |
| 12.68 | 6.97 | s | | 12.58 | 7.03 | vs | |
| 13.52 | 6.54 | s | | 13.51 | 6.55 | s | |
| 14.22 | 6.23 | w | | 14.32 | 6.18 | m | |
| 22.48 | 3.95 | s | | 22.49 | 3.95 | s | |
| 24.01 | 3.70 | m | | 23.93 | 3.72 | w | |
| 25.38 | 3.51 | vs | | 25.38 | 3.51 | vs | |
| 25.96 | 3.43 | m | sh | 26.05 | 3.42 | s | sh |

The invention claimed is:

1. A hydrocarbon conversion process is selected from the group consisting of alkylation, isomerization, olefin dimerization and oligomerization and dewaxing comprising contacting a hydrocarbon stream with a crystalline microporous zeolitic composition at hydrocarbon conversion conditions to give a converted product, the crystalline zeolitic microporous composition having a three-dimensional framework composed of at least tetrahedral SiO$_2$ units and an empirical composition on an anhydrous basis expressed by the empirical formula of:

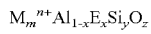

$$M_m^{n+}Al_{1-x}E_xSi_yO_z$$

where M is at least one exchangeable cation selected from the group consisting of hydrogen ion, alkali, alkaline earth, and rare earth metals, "m" is the mole ratio of M to (Al+E) and varies from 0.05 to about 10.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation:

$$z=(m \cdot n+3+4 \cdot y)/2$$

and is characterized in that it has the x-ray diffraction pattern having at least the d-spacings and intensities set forth in Table B:

TABLE B

| 2θ | d (Å) | I/Io % |
|---|---|---|
| 7.45-7.72 | 11.86-11.44 | m-s |
| 9.35-9.53 | 9.45-9.27 | m-s |
| 12.30-13.00 | 7.19-6.80 | m-s |
| 13.25-13.73 | 6.68-6.44 | m-s |
| 15.20-15.80 | 5.82-5.60 | w-m |
| 21.06-21.62 | 4.22-4.11 | m |
| 22.16-22.62 | 4.01-3.93 | m-vs |
| 23.73-24.06 | 3.75-3.70 | m |
| 25.15-25.44 | 3.54-3.50 | vs |
| 25.51-25.95 | 3.49-3.43 | m-vs |
| 28.40-28.57 | 3.14-3.12 | m |
| 30.55-31.15 | 2.92-2.87 | m |
| 49.70-50.40 | 1.83-1.81 | w-m. |

2. The process of claim 1 where M is selected from the group consisting of Li, Na, K, Cs, Ca, Ba, Sr, La and Yb.

* * * * *